Figure 1:
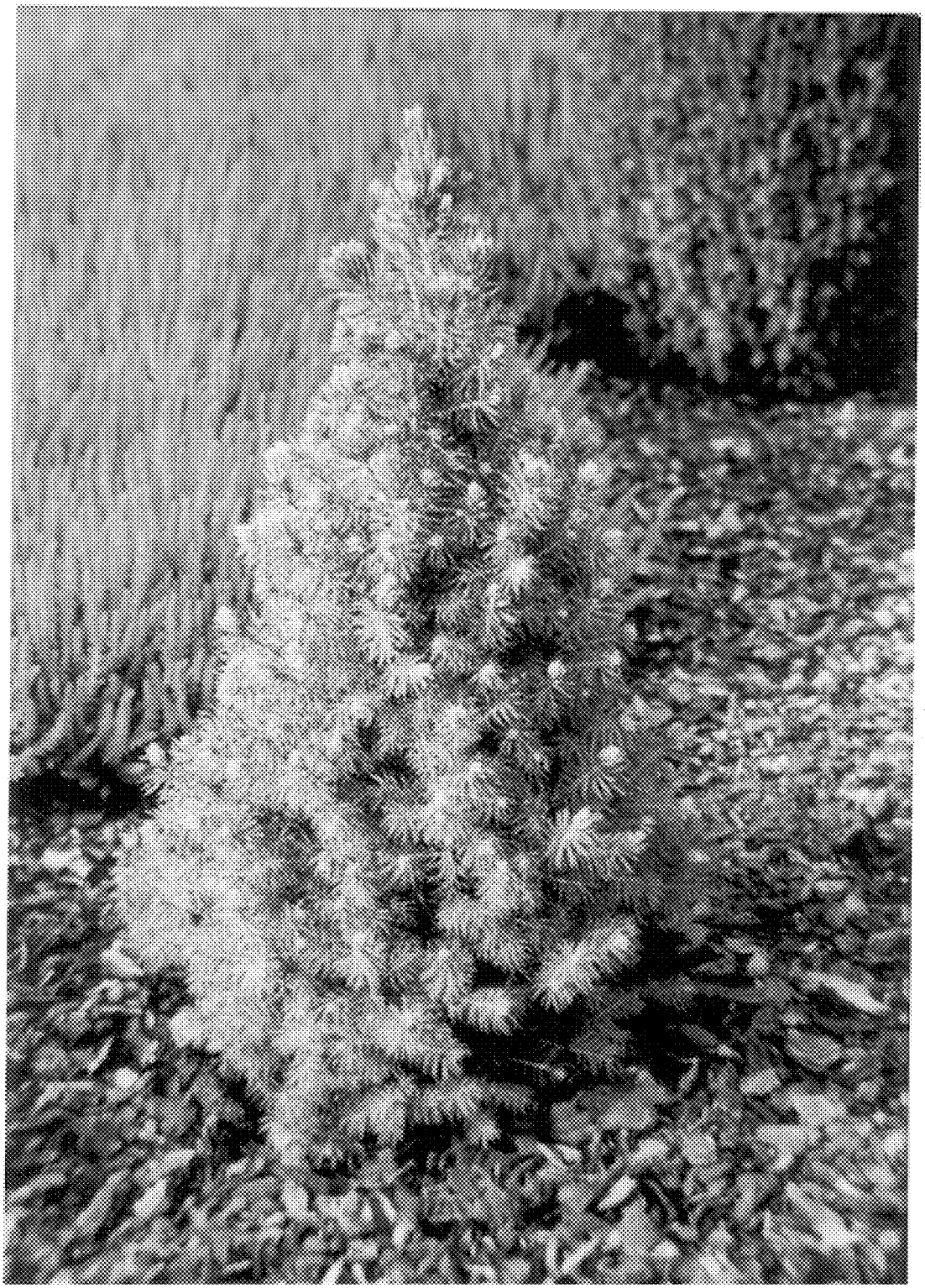

US00PP11473P

United States Patent [19]

Bos et al.

[11] Patent Number: Plant 11,473

[45] Date of Patent: Aug. 8, 2000

[54] PICEA GLAUCA PLANT NAMED 'HAAL'

[75] Inventors: Richard Bos, Hagthorne Cottage Nurseries, Lucas Green Road, West End Woking Surrey, GU24; Isaac Bos, deceased, late of Surrey, both of United Kingdom, by John David Griffiths, executor

[73] Assignee: Richard Bos, West End Woking Surrey, United Kingdom

[21] Appl. No.: 08/980,818

[22] Filed: Dec. 12, 1997

[51] Int. Cl.[7] ..... A01H 7/00

[52] U.S. Cl. ..... Plt./213

[58] Field of Search ..... Plt./213

[56] References Cited

PUBLICATIONS

Huxley, ed., 1992, The New Royal Horticultural Society Dictionary of Gardening, The MacMillan Press Ltd., London, pp. 570–571.

*Primary Examiner*—Howard J. Locker
*Attorney, Agent, or Firm*—Foley & Lardner

[57] ABSTRACT

A new and distinct plant of *Picea glauca* named 'Haal', characterized by its unique blue needle-like foliage and dwarf form.

1 Drawing Sheet

The present invention comprises a new and distinct cultivar of dwarf conifer of *Picea glauca,* with the genus being a member of the pinaceae family. The new cultivar is known by the cultivar name 'Haal'.

Plants within the species are known for their beauty, and frequently grow to as high as nearly 100 feet. However, the cultivar 'Conica', an unpatented cultivar, is a dwarf, conical form of the species, and is frequently used for accent plants due to its dwarf characteristics. The dwarf form is alternatively referred to botanically as *Pinaceae glauca var. albertiana.*

The new cultivar 'Haal', was discovered as a naturally occurring mutation on a portion of a plant of 'Conica' by the inventors in a nursery in Surrey, England. The new cultivar was immediately recognized due to its blue needle-like foliage, and the plant also expressed the vigor and hardiness of its parent.

The new cultivar was first asexually produced by the inventors in Surrey, England by taking cuttings from the naturally occurring mutation. The progeny of both the first and subsequent generations of asexual propagation have clearly established that the unique combination of characteristics as herein disclosed for the new cultivar are fixed and retained through successive generations.

The new cultivar has not been observed under all possible environmental conditions. The phenotype may vary significantly with variations in environment such as temperature and light intensity, without, however, any variance in the genotype.

The following traits have been repeatedly observed and are determined to be basic characteristics of the cultivar, which in combination distinguish the cultivar from others of the species:

1. The truly blue foliage is unique and immediately distinguishes the new cultivar from its parent and other specimen plants of the species.

2. The new plant displays the vigor and hardiness of its parent, and is winter hardy throughout the British Isles.

3. Although the new cultivar has a vigorous habit, it has exhibited a rate of growth equal to approximately one-half that of its parent. This enhances the dwarf nature of the cultivar and consequently its value as a specimen plant.

4. The small, pinnate blue needle-like foliage makes an excellent display year round, although the foliage color is at it best from April to early July. During the winter months, the foliage tends toward a more greyed-green color.

5. The new cultivar thrives best in full sun and well drained soil with a pH of 6.5 to 7 in conditions that are not too dry.

Although the vigor, hardiness and small pinnate needle-like foliage of 'Haal' are similar to its parent 'Conica', Table A shows a more meaningful comparison to the cultivar *Picea glauca* 'Gnom'.

TABLE A

| | *PICEA GLAUCA* 'HAAL' | *PICEA GLAUCA* 'GNOM' |
|---|---|---|
| Plant Habit | Dwarf Upright Conical Habit | SAME |
| Plant Size | 60 CM HT 25 CM SP | 50 CM HT 35 CM SP |
| Root System | Fibrous | SAME |
| Pest & Decease Susceptibility | Shows a Susceptibility to Red Spider Mite | SAME |
| Leaf Arrangement | Acicular, Imbricate Entire Needle Like Foliage | SAME |
| Leaf Length | 10 MM | 12 MM |
| Leaf Width | 1 MM | 0.75 MM |
| Leaf Margins | Entire | SAME |
| Leaf Apex | Apiculate | SAME |
| Leaf Base | Acuminate | SAME |
| Branch | Level to ascending | Ascending |
| Bud | RHS greyed orange 177A | RHS greyed orange 174B |
| Bark | RHS greyed orange 168D to RHS greyed orange 167D | RHS greyed orange 173D to RHS greyed orange 173A |
| Foliar Color | Summer RHS blue green 119B | Summer RHS greyed green 191A |
| Foliar Color | Winter RHS greyed green 189B | Winter RHS greyed green 191B |

The color photographic drawing comprising FIG. 1 shows a typical specimen plant of 'Haal' growing in a border setting.

The following is a detailed description of the new cultivar based on plants grown in Bressingham, England. All color determinations are based on The Royal Horticultural Society Colour Charts.

Plant:

*Origin.*—A mutation from *Picea glauca* 'Conica'.

*Habit.*—Dwarf, upright conical growth, with the growth rate being approximately half the growth rate of the parent cultivar.

*Size.*—Mature plants are 60 cm. in height with a spread of 25 cm.

*Root system.*—Fibrous.

*Plant vigor.*—The new cultivar shows stable and healthy growth throughout Great Britain.

*Hardiness.*—Winter hardy throughout the British Isles. The plant has not been fully tested for maximum summer tolerance above 32° C. (90° F.).

*Bud.*—Slightly resinous and conical in shape; grey-orange in color, R.H.S. 177A.

*Bark.*—Slightly resinous; grey-orange in color, R.H.S. 168D, which changes to R.H.S. 167D as it matures.

*Branches.*—Horizontal or ascending with upward growing tips.

Foliage:

*Arrangement.*—Acicular, imbricate, entire needle-like foliage.

*Type.*—Conifer.

*Texture.*—Stiff, foliage surfaces smooth and dull.

*Length of needles.*—10 mm.

*Width of needles.*—1 mm.

*Margins.*—Entire.

*Apex.*—Apiculate.

*Base.*—Acuminate.

*Color.*—Mature foliage in spring, summer and fall is 119B, with the color being most vivid from April to early July; in winter, needle color becomes a more greyed-green 189B.

*Resistance to pests and disease.*—The plant would show a susceptibility to Red Spider mite, which is common to all *Picea glauca* varieties. The new cultivar shows no more susceptibility than other varieties.

*Other significant characteristics.*—The plant is sterile; therefore, no cones will form or set.

It is claimed:

1. A new and distinct plant of *Picea glauca* named 'Haal', as illustrated and described.

* * * * *